(12) United States Patent
Chaves et al.

(10) Patent No.: US 9,039,416 B2
(45) Date of Patent: May 26, 2015

(54) SPLINT ABUTMENT OVER OSSEOINTEGRATED IMPLANT AND COMPENSATORY SLANTED COPING

(75) Inventors: Branca Fraga de Resende Chaves, Belo Horizonte (BR); Maria Auxiliadoro Mourão Martinez, Belo Horizonte (BR); Luciana Silva Colepícolo, Belo Horizonte (BR)

(73) Assignee: ITP—INSTITUTO DE TECHOLOGIA E PESQUISA LTDA, Belo Horizonte (BR)

( * ) Notice: Subject to any disclaimer, the term of this patent is extended or adjusted under 35 U.S.C. 154(b) by 485 days.

(21) Appl. No.: 12/094,861

(22) PCT Filed: Nov. 3, 2006

(86) PCT No.: PCT/BR2006/000243
§ 371 (c)(1),
(2), (4) Date: Jul. 17, 2008

(87) PCT Pub. No.: WO2007/059595
PCT Pub. Date: May 31, 2007

(65) Prior Publication Data
US 2008/0293012 A1    Nov. 27, 2008

(30) Foreign Application Priority Data

Nov. 23, 2005 (BR) ...................................... 0505827
Oct. 2, 2006 (BR) ...................................... 0505827

(51) Int. Cl.
*A61C 8/00* (2006.01)

(52) U.S. Cl.
CPC ................. *A61C 8/005* (2013.01); *A61C 8/006* (2013.01); *A61C 8/0068* (2013.01); *A61C 8/0071* (2013.01); *A61C 8/0077* (2013.01)

(58) Field of Classification Search
CPC .... A61C 8/0018; A61C 8/0051; A61C 8/005; A61C 8/007; A61C 8/006
USPC ........... 433/172–176, 201.1, 202.1, 215, 220, 433/221
See application file for complete search history.

(56) References Cited

U.S. PATENT DOCUMENTS

| | | | | |
|---|---|---|---|---|
| 4,522,596 A | * | 6/1985 | Ashkinazy | 433/173 |
| 4,907,969 A | * | 3/1990 | Ward | 433/173 |
| 4,997,383 A | * | 3/1991 | Weiss et al. | 433/176 |
| 5,102,336 A | * | 4/1992 | Linkow | 433/176 |

(Continued)

*Primary Examiner* — Heidi M Eide
(74) *Attorney, Agent, or Firm* — Remenick PLLC (57) ABSTRACT

A splint abutment placed on osseointegrated implant for supported prosthesis rehabilitation made of several materials, without restrictions, is provided. This permits the placement of two prosthetic crowns over a single implant with two pins or possibly one and the divergent marginal or cervical girdle, thus providing better biomechanics, marginal sealing, occlusal stability, aesthetics and hygiene maintenance of prosthesis. The shape and contour of the splint abutment provide harmonious distribution and absorption of functional load. Further, a dispositive is provided as a specific piece made of material, without restriction, for fitting between the implant and the splint abutment, which will determine the compensatory and corrective slant adjusting the position of the "abutment" according to the required correction of rotational and multidirectional angulations of the implants for correct rehabilitation. The above-described elements are believed to assure greater predictability of the results.

9 Claims, 4 Drawing Sheets

(56) References Cited

U.S. PATENT DOCUMENTS 5,571,015 A * 11/1996 Siegmund .................... 433/173
5,674,069 A * 10/1997 Osorio .......................... 433/172
5,810,592 A *  9/1998 Daftary ......................... 433/173
5,829,977 A * 11/1998 Rogers et al. ................. 433/172

* cited by examiner

SPLINT ABUTMENT OVER OSSEOINTEGRATED IMPLANT AND COMPENSATORY SLANTED COPING

The present invention is related to a splint abutment for dental a prosthesis that can be made of titanium, gold, carbon, chromium-cobalt, tilite, zirconium, niobium, alumina, and other similar materials, without restriction. It is a splint abutment for implant-supported prosthesis that makes it possible to place two prosthetic crowns over a single implant, thus providing better biomechanics, normal dental function, good aesthetics and hygienic cleaning of prostheses. This invention offers superior resistance of the abutment, lasting aesthetics and a reduction in clinical time, assuring more predictable results.

The aesthetic and functional necessities of lost teeth replacement have been the primary focus in oral rehabilitation. The introduction of the osseointegrated implants increased the possibility of supplying fixed, predictable and functional restorations, mainly in extensive edentulous sites.

The objective of teeth replacement treatment initially concentrated its function and success on the medium and long-term, but new necessities, have brought about discussions and more appropriate treatment planning, providing greater predictability in the final results.

Innovations in technique are necessary so that it has greater functional, aesthetic and biomechanical suitability to the patient's needs, a factor for which the new features introduced by the present invention are so important and justify the protection of the herein described creation.

Currently, the dental osseointegrated implants offered by the technology available in the market receive a single abutment on which a single crown element is placed. In the majority of cases, an inlay splint prosthetic bar is made, and/or a metallic infra structure fused and welded, joining two or more osseointegrated implant abutments, according to the planning of the edentulous site. This inlay splint procedure presents some disadvantages, such as the difficulty in cleaning, the aesthetic problems due to the absence of the prefabricated "abutment" with sinuous format, that follows gingival contour and that provides a more flattened in the mesiodistal direction and lengthened in the buccolingual direction and presents greater similarity to the form of a natural tooth, unlike those currently in the market.

Another disadvantage in the current technique is the difficulty in attaining total passivity of the metallic structure, whose welding points do not always provide total precision in the meeting of the inlay splint blocks, perhaps causing tension that will be transmitted to the implants. Such tension concentrates in the neck of the implant, and it could cause bone loss increase in the periimplant region in the medium or long-term, and, as a consequence, the possible loss of the implant itself or of the implant abutment screw, either by breaking, unscrewing or becoming damaged.

The existence of a similar technology to the one presented by the invention described herein was not verified in searches made in patent databases. The state of the art does not possess similar solutions to the present invention for the use in prosthesis on osseointegrated implants.

The modalities offered currently present single pins with cylindrical formats that bring biomechanical and aesthetic limitations, since they do not follow multidimensionally the contour of the profile of the gingival emergency, which causes a concentration of stress on the implant neck, which could cause greater bone loss in the surrounding area, due to the fact that the pins are single.

The cylindrical format of the available abutment in the state of the technique provides less nesting stability and retention of the prosthetic crown, compared to the innovation described herein. This hinders a uniform motion of the normal dental function forces in the longitudinal direction of the implant, as occurs in the resulting forces of a natural tooth, which could also cause stress concentration in the neck of the implant and bring about bone loss the surrounding area.

All the disadvantages identified above have serious consequences in the effectiveness of the treatment, in the medium and long-term.

In biomechanical terms, the divergences of forces from the normal dental function, resulting from the cylindrical shape of the abutment, could limit the success of clinical solutions, as well as presenting a shape that favors the accumulation of bacterial plaque due to great difficulty of hygienic cleaning.

The existing patents in this technological area, identified in the search carried through in the patents databases, do not solve the existing problems.

The invention patent BR PI9602881-5, for example, presents a thin profile dedicated to very sensitive bone structures, in order to keep the temporary prosthesis attached throughout the process of osseointegration of the definitive implants. The patent of utility model MU7801874-9 is designed to make it easier to implant the prosthesis with a fast and safe attachment to the bone. Its object consists of a cylindrical piece of pure titanium, with a highly polished external ring band at one end, thus better adapting to the gum, and a threaded blind bore, centered in the longitudinal direction, which is larger and hexagonal in the apical third, facilitating the fitting of proper tools for threading the implant in the bone. This arrangement allows greater stability in applying and setting the prosthesis, with the rest of the piece made of a body with external threads, with a surface treated with jet-sprayed aluminum oxide, thus increasing the contact surface for a better interface through the osseointegration.

However, the mentioned patents still do not solve various existing problems in the state of the technique, as for example, the problem of patients with edentulous sites of between 9.7 mm and 13.8 mm. Nor do they establish the ideal passivity conferred through the perfect fit of the abutment in the neck of the implant, as occurs in pre-manufactured abutments. Nor do they eliminate welding points as essential factor in the total passivity of the inlay splint or welded prosthetic crowns with the maximum precision of adaptation of the prosthetic crowns.

The patent of utility model BR MU7400850-1 presents an apparatus for osseointegrated implant consisting of tools and pieces that assist in a fast installation and setting of teeth.

Another patent of utility model BR MU7900158-0 shows a biocompatible and osseointegrated plate for bone setting using screws, designed to speed up the reconstitution and the osseointegration, thus preventing rejection, providing better stabilization, preventing its withdrawal and minimizing, in some cases, the patient's loss of mobility.

However, once again, these patents leave some problems in the state of the technique unsolved, as for example the frequent problem of not providing a suitable emergency profile, similar to natural teeth, and to cause aesthetic difficulties, mainly in the buccal hygienic cleaning.

The procedure widely used today is to make two implants that each receives a dental abutment and a prosthesis, since for each implant of regular platform of 4.1 mm, 7.0 mm is needed between the fixed implant.

There are, however, circumstances when the edentulous site is located between 9.7 mm and 13.8 mm, or there are anatomical defects or prosthetic or surgical planning errors, and as a result there is not space or the necessary conditions for two implants. The alternative commonly used is to make a larger prosthesis implant, or to leave an element hanging (cantilever), which presents functional, biomechanical and aesthetic problems. Another alternative is to adopt a fixed prosthesis, using tooth-implant union. However, it is very controversial. Using the cantilever, as with the state of the technique, the prominent bone overload is clear and the probable future perimplantitis caused by the bone overload, which could expose the inter-bone part of the implant in contact with the subgingival microbiota, possibly causing future implant loss.

It is therefore clear that the existing technologies still provide no solution for some problems related to the dental implant, as indicated.

The great spacial difference that exists between the perimeter of the normal dental function plane of the prosthetic crown and the diameter of the implant or of its neck, has always caused problems in the aesthetic as well as in the hygienic cleaning because it does not provide an appropriate emergency profile, one that has a shape that makes it possible to format or to follow the triangular contour of papillas and of the interproximal crenas. The rose aesthetic of the gum should hug the prosthetic white crown to achieve the best result of aesthetic excellence in implant-supported work.

To solve such problems, the invention described here presents a splint abutment that makes it possible to place two dental elements in a single implant, thus providing better normal dental function, aesthetic stability and oral hygienic maintenance.

The innovation described here provides greater nesting stability and retention of the prosthetic crown, bringing about better directing of normal dental function forces in the axial of the implant, as it occurs with natural tooth forces, where the tensions are equally distributed, diminishing the concentration of tensions on the neck of the implant.

The new design presented by the invention described here allows greater stability, retention and directing of prosthesis forces for the axial forces of the implant, since the adaptation of the prosthetic crown occurs in the divergent girdle and not in the neck of the implant, thus presenting more favorable and appropriate biomechanical properties by allowing an emergency profile more similar to the natural tooth.

The present invention provides better marginal sealing, as well as better hygienic cleaning, since the nesting of the prosthetic crown occurs above of the implant neck, in the divergent girdle of the pre-manufactured abutment, which can still be re-preparable, adjusting the prosthetic emergency profile according to the contour shape of the gingival architecture.

The splint abutment has parallel, slightly flared pins for the normal dental function, with convergence degree of 6° to 9°, and they form angles between 30° and 60° with the insertion axis of the implant, conforming with the emergency profile of the gingival papilla.

It presents a milling area of 1.0 mm to 5.0 mm in the longitudinal direction, to guide the insertion axis of the prosthetic crown, as well as to confer greater stability and retention, more naturally characterizing the contact point of the inlay splint crown.

There is also a chanfer area or shoulder with a rounded axio-cervical angle in all the perimeter of the cervical edge, determined by sustaining periodontium.

The biomechanical possibilities of the invention allow better occlusal stability, since the shape and contour of the abutment partially distribute and absorb the occlusal load for the axial forces.

The abutment possesses a neck or divergent marginal girdle of adjustable height of 1.0 mm to 8.0 mm, and changeable perimeter between 4.5 mm and 14.0 mm, in the mesio-distal direction and buccolingual perimeter of 4.0 mm to 9.0 mm, from where two pins protrude with height, also adjustable, of between 2.0 mm and 13.5 mm, and changeable diameter of 1.0 mm to 8.0 mm, according to the edentulous site. These pins are parallel to themselves, slightly flared for normal dental function, with a chanfered area in all its cervical ending, that is, bevel deep chanfer or shoulder with rounded axio-pulpar angle, which can be pre-manufactured and repreparable for individualization of the piece according to the architecture of the gingival contour. Between the pins there is a narrow channel or milling area that can be located either in the vestibular or in the lingual position, to confer greater retention and stability to the splint abutment.

In the central portion of the abutment there is an open area where the screw of the abutment is fixed for cases of internal hexagon implant, external hexagon, or internal octagons, and a totally compacted area for a Morse cone and cold welding implants.

The splint abutment, object of the present invention, can, when necessary, be separated into two parts, separating the pins from the marginal girdle and then fitting them together to assemble them.

The dismemberment of this abutment can also occur in the splint abutment coupling base, in cases of inclination correction of the implant in the mesio-distal or buccolingual directions, rotationally, where the use of a connected cylindrical part is necessary, that is, a compensating slanted cap that provides an inclined plane, varying from between 0° to 35°, to adjust the "abutment" position according to each case, providing greater possibility for correction of the rotational angles. In specific buccolingual bone defects, for example, where there is the need of angle correction, such defects can be corrected through the slanted coping.

The compensatory slanted coping, which will be fitted between the implant and the splint abutment, is characterized by being a specific piece made of the same, material as the abutment, with a perforation where the fixation screw of the "abutment" will pass. The height of the inclination slant can vary in accordance with the angle from between 0° and 35°, rotational, which will determine the compensatory and corrective slant. In the case of the present invention, the screw of the splint abutment must be sufficiently large, in height, to compensate the height of the compensatory slanted coping. The splint abutment provides an opening between the bolts of 2.1 mm to 5.5 mm, designed to make it possible to insert the axis of the abutment screw, when the coupling part is needed, that is, the compensatory slanted coping. Besides the functional, operational and aesthetic advantages of these alternatives, they also speed up, facilitate and simplify the process of industrial production of the parts, as to reduce its final cost.

For the Morse cone and cold welding cases, the compensatory slanted coping will be connected in the vertical direction, with the same inclination compensation varying from between 0° and 35°.

The splint abutment, object of the present invention, also presents the inclination compensation of the implants set on the bone ridge, with a single part, with a variation between 10° and 35° with the implantation insertion axis. The multi-dimensional angled splint abutment still offers the alternative of being repreparable, accordance to the availability of the gingival architecture, and offers a flexibility of shape for greater effectiveness of the of the implant result, as well as for greater comfort and patient adaptation.

The pins are parallel, slightly flared for the occlusal and form angles between 30° and 60° with the neck, in accordance with the emergency profile of gingival papilla. They possess a chanfer area, or deep chanfer, or shoulder with axio-cervical angle rounded in its entire perimeter, following the edge of the profile of natural emergency provided by periodontium support.

The peripheral and internal gingival contour is obtained by means of making a prefabricated coping for splint abutment, or by making moldings, for cases of repreparable splint abutments, providing an anatomical contour similar to natural teeth.

The splint abutment can present a narrowing at the base of the cervical divergent brace, in all its perimeter of 0.7 mm to 2.0 mm for gingival biological space between the platform of the implant and the splint abutment.

The present invention innovates the state of the art, since it offers a product that makes it possible, in a single osseointegrated implant, whether of external hexagon, internal hexagon, internal octagon, Morse cone and cold welding, to place two dental elements conjugated or inlay splint, with the option for cemented or screwed prosthesis in cases of edentulous sites up to 15.0 mm, for cases that present anatomical or surgical variations that prevent placing two implants.

The invention described here, for its different variations of shape, height and diameter, offers better aesthetic, marginal sealing, oral hygiene maintenance, greater normal dental function stability, total passivity for being free of welding points, as well as a reduction in treatment time and a simplification of the clinical and prosthetic procedures. These advantages lead to an optimization of the surgical and rehabilitation planning, besides obtaining an aesthetic proof, in the way of models, perfect to provide predictability for future prosthetic rehabilitation reconstruction and, above all, to improve the final result, reflected in lower operational costs, as well as better execution of the procedure.

The present innovation also aims to present individualized splint abutments solutions, for the posterior or anterior region, besides corrective abutments according to the positioning or topography of periodontium.

The splint abutments, described here, straight and angled, since they are prefabricated, offer the advantage of eliminating the laboratorial phase of dieing, waxing and scanning that still occurs with the existing products in the state of the technique.

The splint abutment also offers a solution for placing a single element, with wide or small diameter, whose edentulous site is up to 10.0 mm, the mesiodistal or buccolingual, since it provides a much more natural emergency profile, that is, more similar to the original tooth. It also favors proper oral hygiene maintenance and offers much more suitable and satisfactory biomechanical properties. There is, moreover, the possibility of varied positioning of the splint abutment to naturally follow the individualized emergency profile, since it presents adjustable dimensions and chanfers that follow the convex/concavous profile of the gingival tissue.

The new exclusive design of the product, object of the present invention, furthermore offers clinical benefits, since, by means of the marginal sealing, it provides better bacterial protection, besides providing to higher periodontal health for ensuring a more suitable hygienic cleaning, following the gingival architecture.

A further embodiment of the present invention is related to small variations, mainly in relation to the dimensions, and greater detailing of splint abutment and compensatory slanted coping. The product of this additional embodiment makes it possible to place two inlay splint prosthetic elements in a single osseointegrated implant, in edentulous sites of up to 16.0 mm, for cases in which anatomical or surgical variations occur that prevent the insertion of two implants.

The splint abutment provides better marginal sealing, as well as better oral hygiene maintenance; therefore the passive nesting of the splint abutment occurs in the platform of the implant. The adaptation of the prosthetic crown is done above this platform, that is, in the divergent girdle of the prefabricated splint abutment, repreparable. Moreover, it can be adjusted and individualized in accordance with the contour shape and the gingival architecture, adjusting itself to the height of its sinuosity, to the sizes and height of the divergent cervical, buccal and lingual girdle, of 0.5 mm to 10.0 mm, and of the divergent interproximal cervical girdle, from 1.0 mm to 12.0 mm, adjusting the emergency profile of the prosthetic.

The splint abutment has two parallel pins, slightly flared for the normal dental function, with a convergence degree of 4° to 30° with the insertion axis of the prosthetic crown and forming angles of 8° and 60° between themselves, and it is possible to merge them in cases where the edentulous site is less than 10 mm. They have a chanfer area, or deep chanfer, or shoulder with axio-cervical angle rounded along its entire perimeter, following the border of the natural emergency profile presented by periodontal.

The divergent girdle forms angles between 30° and 80° with the axial forces of implant setting, determined by the anatomical contour of the gingival papilla, with the option of using a cemented prosthesis, individualized or not. For cases of screwed prostheses, the splint abutment could be reprepared to directly receive the selected restoring material or even to receive fused ceramics directly in the splint abutment.

There is a milled area between the bolts of 1.0 mm to 5.0 mm in the longitudinal direction, both in the vestibular or in the lingual or both, to guide the insertion axis of the prosthetic crown, as well as to confer greater stability and retention of the crown, rendering the point of contact between the crown more naturally.

The splint abutment possesses a neck or divergent marginal girdle of adjustable height from 1.0 mm to 8.0 mm, and a variable length between 3.0 mm and 14.0 mm both in the mesiodistal and in the buccolingual direction, from where two pins protrude, also with adjustable heights, between 2.0 mm and 13.5 mm, and variable diameter of 1.0 mm to 8.0 mm, determined by the edentulous site.

There is, also in the divergent girdle, a milling area that can be placed either in the buccal or in the lingual or both, to confer greater retention and stability to the splint abutment.

In the central portion of the splint abutment there is an open area where the splint abutment screw is fixed, for cases of internal hexagon implant, external hexagon, internal octagon, internal duodecagonous, non-restrictive, and completely compacted for implant area of the Morse cone type and cold welding or, even, a single body implant, also non-restrictive.

In some cases, the open area could be differentiated by being lingualized in relation to the parallel pins in the anterior elements, and in the posterior elements, for overlap cases.

The open area, where the splint abutment screw is fixed, can also be differentiated, because it coincides with the positioning place of one of the parallel pins, allowing an extension of up to 55 mm of the divergent girdle, both for mesial and for distal.

In some cases, as buccolingual bone defects, setting inclined implants, for example, where there is the need for angle correction, these can be corrected through the angled compensatory slanted coping.

The compensatory slanted coping, which will be fit between the implant and the splint abutment, is characterized for being a specifically made piece with the same material of the abutment, non-restrictive, with a perforation through which the screw of the "abutment" setting will pass. The height of the compensatory slanted coping can vary in accordance to the angle between 0° and 50°, rotational, which will determine the compensatory and corrective slant. In the case of the present invention, the screw of the splint abutment must be large enough, in height, to compensate the height of the compensatory slanted coping. The splint abutment presents an opening between the bolts of 2.1 mm to 5.5 mm, designed to make it possible to insert the axis of the abutment screw, when the coupling piece is needed, that is, of the inclination plane. Besides the functional, operational and aesthetic advantages of these alternatives, they not only speed up, facilitate and simplify the process of industrial production of the pieces, but they also reduce the final cost.

For the Morse cone and cold welding cases, the compensatory slanted coping will be connected in the vertical direction, with the same compensation of inclinations varying from 0° to 50°.

The splint abutment, object of the present invention, also presents the inclination compensation of the implants set on the bone ridge, in a single piece, with variation between 10° and 60° with the implant insertion axis. The multidimensional angled splint abutment furthermore provides the alternative of being repreparable, offering a shape flexibility to allow greater effectiveness of the implantation result, as well as greater comfort and adaptation for the patient.

The peripheral and internal gum contour of the prosthetic crown is obtained by making the pre-manufactured coping for splint abutment, or by making moldings. For the cases of repreparable splint abutments, it provides anatomical contour, similar to natural teeth or even by means of sculpture and fused ceramics directly on the splint abutment, eliminating molding, casting and welding stages, reducing the laboratorial clinical time as well as final cost.

The present invention can be better understood by means of the presented figures, where.

In accordance with FIGS. 1-4, one can observe that the splint abutment, according to the invention, comprises a divergent girdle 13 on which is placed a pin support element 12. The pin support element 12 is formed by the pin base 23 and by two pins 22a, 22b, which are frustro-conical, parallel between them and protruding toward the occlusal direction. In addition, the taper of said pins 22a, 22b is defined by an angle β (FIGS. 2 and 3) between 4° and 30°. Pins 22a, 22b are arranged on the pin base 23, whose shape is complementary to the top of the divergent girdle 13. The divergent girdle 13 and the pin support element 12 can be separated into two parts, when necessary. In another form of execution (FIG. 4a), the divergent girdle 13 and the pin support element 12 comprise a single piece, which is made at the manufacture procedure.

Figure 1:
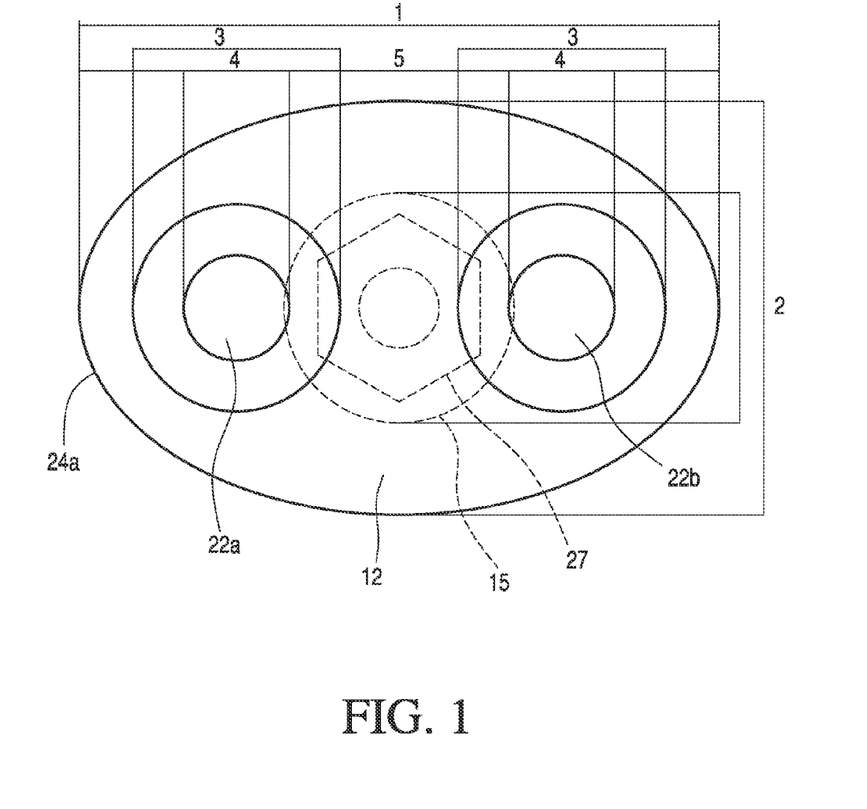
FIG. 1 shows the plant or view from above the implant where: (1) is the mesiodistal distance that varies from 4.5 mm to 14.0 mm; (2) is the buccolingual distance that varies from 4.0 mm to 9.0 mm; (3) is the diameter of the base of the pins that varies from 2.5 mm to 6.0 mm; (4) is the diameter of the top of the pins that varies from 2.0 mm to 4.0 mm; (5) is the space between the two the pins that varies from 2.1 mm to 5.5 mm.
Figure 2:
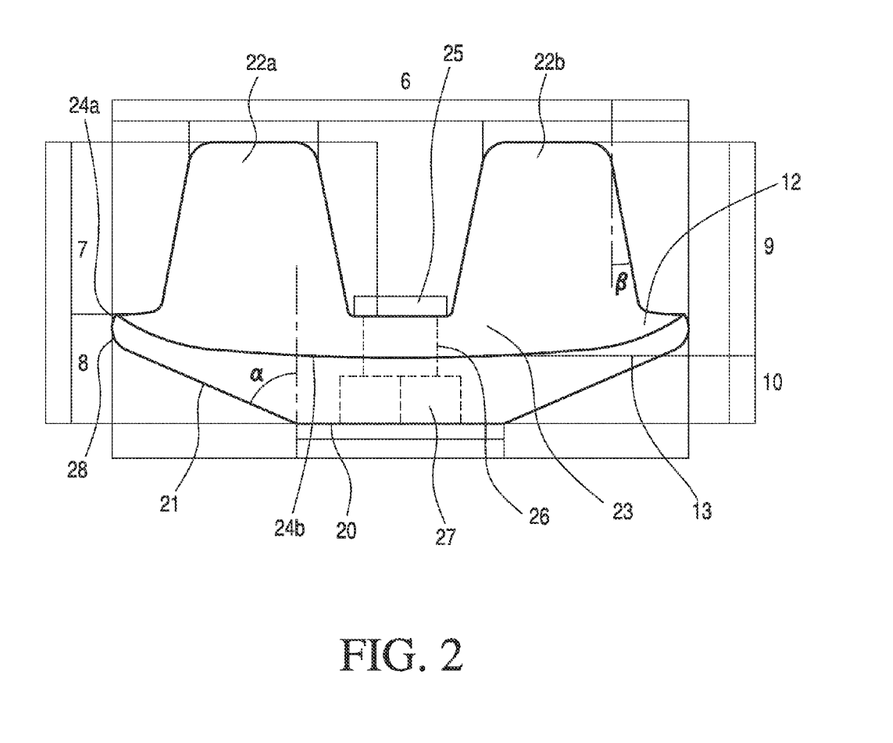
FIG. 2 shows the front view of the implant where: (6) is the mesiodistal distance that varies from 4.5 mm to 14.0 mm; (7) is the height of the pins from 2.0 mm to 13.5 mm; (8) is the height of the cervical interproximal divergent girdle that varies from 1.0 mm to 6.0 mm; (9) is the abutment height that varies from 4.0 mm to 14.5 mm; (10) is the height of the buccal and/or lingual divergent cervical girdle that varies from 1.0 mm to 5.0 mm.
Figure 3:
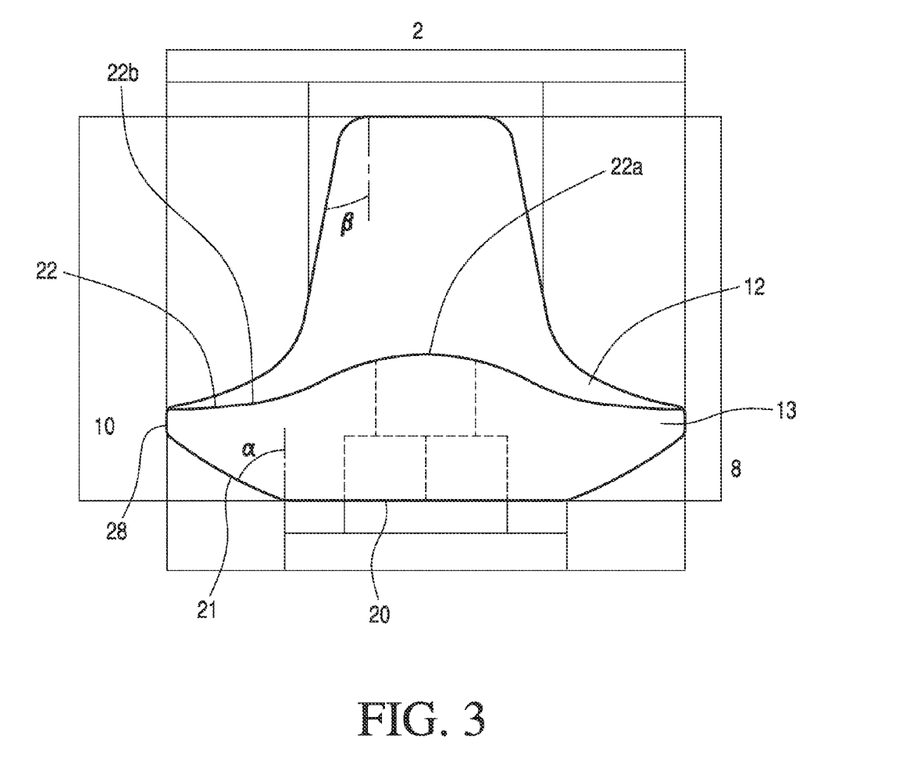
FIG. 3 shows the lateral view of the implant where: (2) is the buccalingual distance that varies form 4.1 mm to 9.0 mm; (8) is the height of the divergent cervical girdle that varies from 1.0 mm to 6.0 mm; (10) is the height of the buccal and/or lingual divergent cervical girdle that varies from 1.0 mm to 5.0 mm.

In turn, the divergent girdle 13 presents an overall shape of an oblong cup with the edge 24a, 24b being shaped as the emergency profile of contour shape, which reproduces the concave/convex emergence profile of the gingival architecture in natural teeth, where the prosthetic crown is laid. Said edge is "higher" 24a in the mesio-distal axis, and "lower" 24b in the buccolingual axis, with the length of the axis in the mesio-distal direction (FIG. 2) being greater than the length of the axis toward buccolingual (FIG. 3). Thus, the section of the divergent girdle 13 in the horizontal plane shows the shape of an ellipse (see FIG. 1), which may appear more triangular according to the dental anatomy of the anterior region, following the parabola of the dental arch and also for prosthetic compensation (overlaps) of the variations in positioning the implants.

The divergent girdle 13 presents a connection 20 intended to be fastened to the upper portion of the implant 15. The anatomical contour of the gingival papilla 21 of the divergent girdle 13 protrudes from connection 20 and it is divergent in the occlusal direction, i.e., divergent from the region near the implant platform 15 (i.e. the cervical region) to the edge 24a, 24b of the divergent girdle13. As already stated, the divergent girdle 13 forms an angle α with the occlusal axis (indicated by dashed lines in FIGS. 2 and 3) of the splint abutment, between 30° and 80°. This anatomical contour of the gingival papilla 21 of the divergent girdle may angularly variable, in single pieces, for compensation of tilted implants between 10°-60°, and it can be reparable.

Figures 4A, 4B:
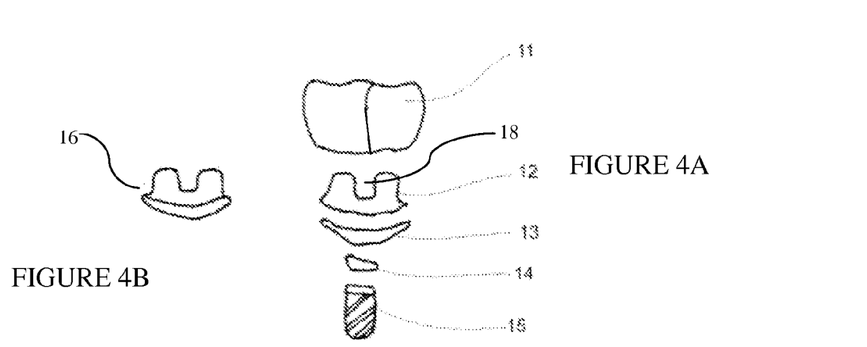
FIGS. 4A-C show the items that make up the splint abutment where: (11) are the prosthetic crowns; (12) are the parallel pins with a milled area (18) there between; (13) is the divergent girdle; (14) is the compensatory slanted coping; (15) is the implant; (16) is the splint abutment and (17a and 17b) are the splint abutments on the implant with and without the compensatory slanted coping; (17a) is the splint abutment, and the two prosthetic crowns, on the implant in the correct position with the compensatory slanted coping and (17b) is without the compensatory slanted coping.
Figure 4C:
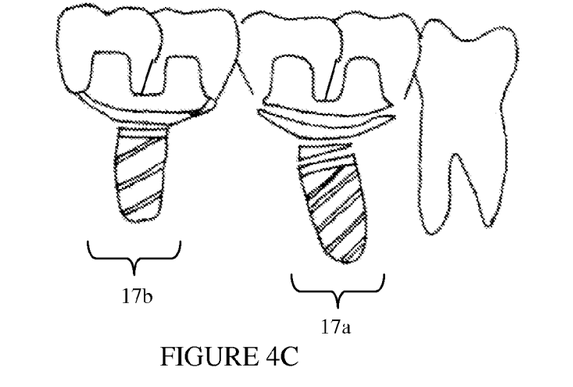

The chamfer area 28 in all the perimeter of the cervical edge of the divergent girdle 13 (above the anatomical contour of the gingival papilla 21) has a beveled conformation. Thus, it is possible to obtain a better marginal sealing between the splint abutment and the prosthetic crown (see FIG. 4).

Finally, the central region of the splint abutment, toward the occlusal/apical direction, has a through hole 26, also known as hollow area, and designed to receive the fastening screw 25 (only the screw head illustrated in FIGS. 2 and 3), which is designed to keep the splint abutment properly fastened to the implant 15. This hollow area 26 can be presented lingualized in anterior elements or in overlap cases.

Number 27 illustrates the hexagonal plug of implant 15. Alternatively, and according to known techniques, a screw and a respective through hole may be located in one of the pins 22a, 22b, for cases of decentralized fixations. In another embodiment, in the cases of Morse cone or cold weld types, there is a specific connection, where screw 25 is not used and through hole 26 does not exist.

Therefore, with broad and immediate application in the implant-support area, the invention presented here justifies its protection for both its innovative character and for the great contribution to the technological development in the medical-odontologic sector, since this invention can also be used for osseointegrated implants in other medical areas.

The invention claimed is:

1. A pre-manufactured and adjustable splint abutment comprising:
   two pins, one cervical divergent girdle, and one splint abutment screw forming a single abutment to be placed over a single osseointegrated implant;
   wherein the two pins are adapted to receive two prosthetic crowns and the splint abutment has an area in which the splint abutment screw is fixed, said splint abutment screw adapted to promote coupling between the splint abutment and the osseointegrated implant through an internal connection or an external connection of the osseointegrated implant, the internal or external connection being one of an internal or external hexagon, an internal octagon or an internal duo-decagon, the splint abutment being adapted to be fixed in an edentulous site up to 16.0 mm long;
   wherein the cervical divergent girdle has a sinuous and oblong shape that follows a concave/convex profile of gingival tissue architecture and has heights ranging from 0.5 to 10.0 mm in a buccal portion and a lingual portion and ranging from 1.0 to 12.0 mm in an interproximal portion, and a variable length of between 3.0 and 14.0 mm both in the mesiodistal and in the buccolingual directions, and the cervical divergent girdle forms angles between 30° to 80° with axial forces of the single osseointegrated implant; and
   wherein the two pins protrude from a contour of the cervical divergent girdle, the two pins each have adjustable heights of between 2.0 and 13.5 mm, are spaced apart at a distance of 2.1 to 5.5 mm, have a convergence degree of 4° to 30° with an insertion axis of the two prosthetic crowns, and have a variable diameter of 1.0 to 8.0 mm, as determined by the edentulous site.

2. The splint abutment, according to claim 1, wherein the splint abutment is adapted for nesting on a platform of the single osseointegrated implant and the two prosthetic crowns, are positioned on a margin of the cervical divergent girdle of the splint abutment, which includes a chamfered area along a cervical edge of the cervical divergent girdle.

3. The splint abutment, according to claim 1, wherein a narrowing of the cervical divergent girdle along an entire perimeter thereof, from 0.7 to 2.0 mm provides a gingival biological accommodation between the implant and the splint abutment and a milled area positioned in the longitudinal direction, in the vestibular direction, or in the lingual direction, in order to provide greater retention and stability.

4. The splint abutment, according to claim 1, wherein the area in which the abutment screw is fixed coincides with one of the two pins or between them, thereby allowing an extension of up to 5.5 mm of the cervical divergent girdle, for both mesial and distal directions.

5. The splint abutment, according to claim 1, wherein the splint abutment provides a slant compensation for the osseointegration implants, and wherein the slant compensation is adjustable and varies from 10° to 60° with the implant placement axis being in a single piece.

6. The splint abutment, according to claim 1, wherein the splint abutment is adapted to be dismembered into two parts, separating the two pins from the cervical divergent girdle and fitting them together to assemble the splint abutment.

7. The splint abutment of claim 1 wherein the two pins form angles between 30° and 60° with an insertion axis of the implant, and the cervical divergent girdle has one of a chamfer area and a shoulder with a rounded axio-cervical angle in a perimeter of a cervical edge for adaption with the two prosthetic crowns.

8. The splint abutment according to claim 1, wherein the area comprises a differentiated open area adapted to be lingualized in relation to the pins of anterior elements, and for cases of overlap of posterior elements.

9. The splint abutment according to claim 1, further comprising a compensatory slanted coping.

* * * * *

UNITED STATES PATENT AND TRADEMARK OFFICE
CERTIFICATE OF CORRECTION

| | | |
|---|---|---|
| PATENT NO. | : 9,039,416 B2 | Page 1 of 1 |
| APPLICATION NO. | : 12/094861 | |
| DATED | : May 26, 2015 | |
| INVENTOR(S) | : Branca Fraga de Resende Chaves, Maria Auxiliadora Mourão Martinez and Luciana Silva Colepícolo | |

It is certified that error appears in the above-identified patent and that said Letters Patent is hereby corrected as shown below:

On the Title Page, Item (75) Inventors, please change "Maria Auxiliadoro Mourão Martinez" to -- Maria Auxiliadora Mourão Martinez --

On the Title Page, Item (73) Assignee, please change "ITP – INSTITUTO DE TECHOLOGIA E PESQUISA LTDA" to -- ITP – INSTITUTO DE TECNOLOGIA E PESQUISA LTDA --

Signed and Sealed this
Fifteenth Day of March, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 9,039,416 B2 | Page 1 of 1 |
| APPLICATION NO. | : 12/094861 | |
| DATED | : May 26, 2015 | |
| INVENTOR(S) | : Branca Fraga De Resende Chaves | |

It is certified that error appears in the above-identified patent and that said Letters Patent is hereby corrected as shown below:

"On the Title Page, Item (73) Assignee, please change "ITP – INSTITUTO DE TECHOLOGIA E PESQUISA LTDA" to -- ITP – INSTITUTO DE TECNOLOGIA E PESQUISA LTDA --" (as corrected to read in the Certificate of Correction issued March 15, 2016) is deleted and patent is returned to its original state with the applicant & assignee name in patent to read
--(73) Assignee: **ITP—INSTITUTO DE
TECHOLOGIA E PESQUISA LTDA**,
Belo Horizonte (BR)--

Signed and Sealed this
Twenty-eighth Day of June, 2016

Michelle K. Lee
*Director of the United States Patent and Trademark Office*